United States Patent [19]
Schickli et al.

[11] Patent Number: 5,698,714
[45] Date of Patent: Dec. 16, 1997

[54] PROCESS FOR THE PREPARATION OF 9,10-SECOCHOLESTA-5,7,10 (19)-TRIENES

[75] Inventors: Christof Schickli, Castagnola; Mathias Jud, Lugano; Fabrizio Marazza, Novaggio, all of Switzerland

[73] Assignee: Cerbios Pharma S.A., Switzerland

[21] Appl. No.: 678,312

[22] Filed: Jul. 11, 1996

[30] Foreign Application Priority Data

Jul. 11, 1995 [CH] Switzerland ............... 02 042/95-2

[51] Int. Cl.$^6$ ............................................. C07C 401/00
[52] U.S. Cl. .................... 549/332; 549/554; 552/653
[58] Field of Search ............... 552/653; 549/332, 549/554

[56] References Cited

PUBLICATIONS

Kluge, et al, Tetrahedron, 52 (8), pp. 2957–2976 (1996).
Curci, et al, J. Am. Chem. Soc., 116, pp. 8112–8115 (1994).

Primary Examiner—Kimberly J. Prior
Attorney, Agent, or Firm—Burns, Doane, Swecker & Mathis, L.L.P.

[57] ABSTRACT

The invention recites a process for preparing 9,10-secocholesta-5,7,10(19)-trienes of formula (I)

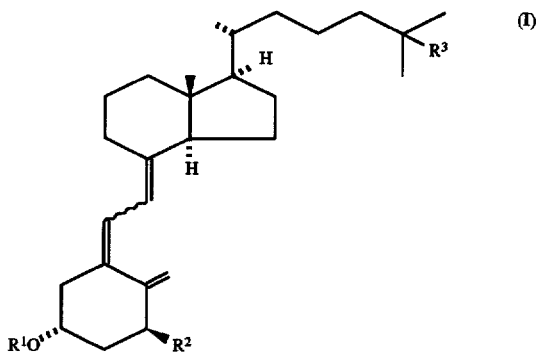

where $R^1$ is hydrogen or a hydroxy-protecting group and $R^2$ and $R^3$ are independently hydrogen or $OR^1$. The compounds are prepared from epoxides of the following formulas

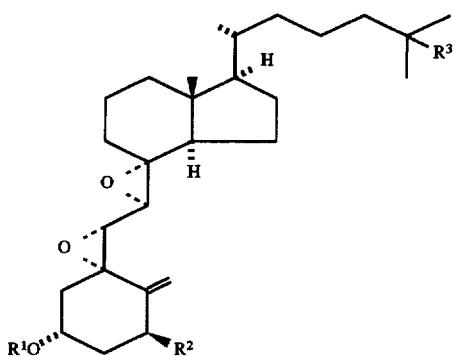

or

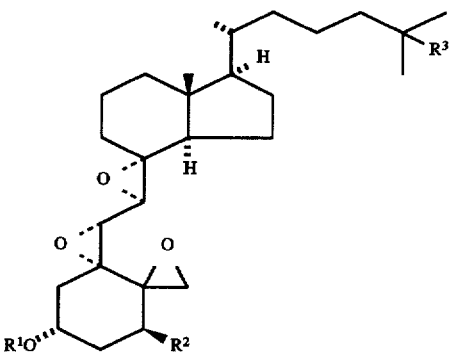

by reaction with a low-valent metal reagent formed by reducing a metal halide, $M(z)X_z$, preferably $WCl_6$.

29 Claims, No Drawings

PROCESS FOR THE PREPARATION OF 9,10-SECOCHOLESTA-5,7,10 (19)-TRIENES

The present invention is directed to a process for the preparation of 9,10-secocholesta-5,7,10(19)-trienes.

The present invention is also directed to a process for the preparation of 5,6:7,8:10(19)-triepoxy-9,10-secocholesta-24-enes.

In addition the present invention is directed to 5,6:7,8-diepoxy-9,10-secocholesta-10(19)-enes and 5,6:7,8:10(19)-triepoxy-9,10-secocholesta-24-enes.

Vitamin $D_3$ of the formula

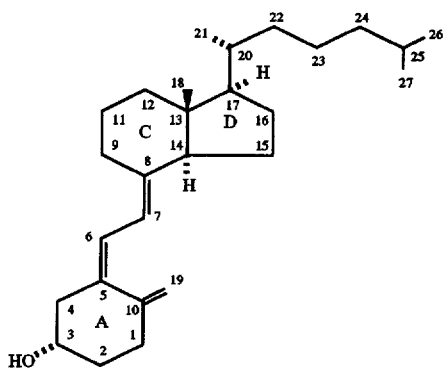

is also named (5Z,7E)-3β-hydroxy-9,10-secocholesta-5,7,10(19)-triene.

Upon the pharmacological meaning of vitamin $D_3$ and its derivatives are published several review articles, see e.g.: Norman, A. W.; Bouillon, R.; Thomasset, M. (Eds), Vitamin D, A Pluripotent Steroid Hormone: Structural Studies, Molecular Endocrinology and Clinical Applications; Walter de Gruter: Berlin, New York, 1994, and references cited herein.

Natural metabolites of vitamin $D_3$ are 25-hydroxy-vitamin $D_3$ and 1,25-dihydroxy-vitamin $D_3$, whereby said dihydroxy compound is responsible for the biological activity.

There were developped several methods in order to prepare synthetically the above mentioned metabolites. Thereby the following fundamental ways were choosen:

1. Derivatisation of steroids. See for example

Barton, D. H. R.; Hesse, R. H.; Pechet, M. M.; Rizzardo, E.J.Am.Chem.Soc.1973,95,2748. (A Convenient Synthesis of 1α-Hydroxy-Vitamin $D_3$).

Barton, D. H. R.; Hesse, R. H.; Pechet, M. M.; Rizzardo, E.,J.Chem.Soc.Chem.Commun. 1974,203. (Convenient Synthesis of Crystalline 1α,25-Dihydroxyvitamin $D_3$).

2. Convergent synthesis be means of a combination of the derivatised A-ring system with the derivatised C/D-ring system. See for example:

Baggiolini, E. G.; Iacobelli, J. A.; Henessy, B. M.; Batcho, A. D.; Sereno, J. F.; Uskokovic, M. R., J. Org. Chem. 1986,51,3098. (Stereocontrolled Total Synthesis of 1α,25-Dihydroxycholecalciferol and 1α,25-Dihydroxyergocalciferol).

3. Direct functionalization of Vitamin $D_3$.

When vitamin $D_3$ shall be functionalized directly, then the triene-system must be protected previously.

According to CH PS 658 050 H. DeLuca used in his 1α-hydroxylation a cyclovitamin $D_3$-methyl ether as protecting group.

The method according to EP 0 078 704 B1 described from R. Hesse uses a Diels-Alder-Adduct of $SO_2$ with vitamin D.

With regard to the introduction of the hydroxy group in position 25 these two methods have the drawback that the side chain must first be degraded and then must again be built up in a modified way.

A known method for the protection of double bonds consists therein, to transform the double bond in an epoxide.

Mono-, di- and tri-epoxides of Vitamin D are known in the literature, but are functionalized neither in position 1 nor in position 25. See for example J. Org. Chem. 1984, 49, 1537, and Monatsh. Chem. 1985, 116, 831 and references cited herein.

R. Curci et al. describes in J. Am. Chem. Soc. 1994, 116, 8112–8115 a one-pot process for the regio-specific hydroxylation of the position 25, combined with the protection of the triene-system as triepoxide.

This method is ideal for the introduction of the hydroxy group in position 25, but presupposes that from the triepoxide the triene-system of vitamin $D_3$ may be regenerated selectively.

But such regeneration methods are not described.

The regeneration of non-conjugated double bonds from non-adjacent epoxides with the reagent $WCl_6$/n-BuLi is described in the literature; see for example K. B. Sharpless et al., J.Am.Chem.Soc. (1972), 94,6538; Journal of the American Chemical Society, Vol. 94, Nov. 18, 1972, pages 6538–6540; Journal of Organic Chemistry, Vol. 57, Nov. 17, 1992, pages 4717–4722; Canadian Journal of Chemistry, Vol. 68, Nov. 1, 1990, pages 153–185 and Journal of the American Chemical Society, Vol. 112, Nov. 12, 1990, pages 4988–4989.

It is an object of the present invention to provide a process for the preparation of in position 1 and/or in position 25 hydroxylated 9,10-secocholesta-5,7,10(19)-trienes.

This process shall include the direct or stepwise regeneration of the triene-system from the triepoxides, prepared for example according to the above mentioned process of R. Curci.

This process shall also include at a stepwise regeneration of the triene-system the possibility to introduce in position 1 a hydroxy group.

This process shall be realizable in a technical simple way and shall comprise not much steps.

It is a further object of the present invention to provide derivatives of vitamin $D_3$, in which the triene-system is protected as triepoxide and which have in the side chain such a functional group, which allows further modifications.

There shall also be provided a process for the preparation of these derivatives.

These objects are obtained with the inventive processes and the inventive compounds.

The first inventive process for the preparation of 9,10-secocholesta-5,7,10(19)-trienes of the formula I

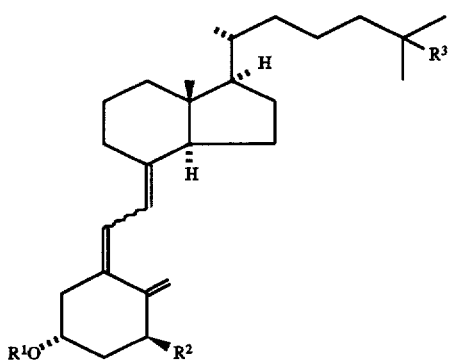

(I)

wherein

R¹ is hydrogen or a protecting group for the hydroxy function, to which R¹ is bound, R² is hydrogen or OR¹, wherein R¹ is defined above, R³ is hydrogen or OR¹, wherein R¹ is defined above, whereby the groups R¹, R² and R³ may be selected independently from each other, is characterized in that in a first step a transition metal halide of the formula II $$M(z)X_z \quad (II)$$

wherein

M(z) is W(VI), Nb(V), Mo(V), Ti(IV), Ti(III) or Fe(III),

X is chloride, bromide or iodide, z is an integer from 3 to 6, is reduced with 1 to z equivalents, preferably 2 to 4 equivalents, of an alkyl metal compound or a metal hydride to a corresponding low-valent metal reagent under an inert gas atmosphere in a waterfree ether or a hydrocarbon, in a second step a compound of the formula III

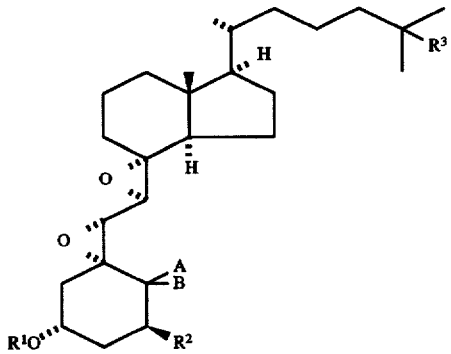

(III)

wherein

R¹, R², R³ are defined above,

A and B taken together are either an epoxide of the formula —(O—CH₂)— or an exocyclic methylene group of the formula =CH₂, dissolved in an above mentioned solvent, is added to the in the first step prepared low-valent metal reagent and is allowed to react, in a third step the so obtained reaction product is worked up and the product of formula I is obtained.

The second inventive process for the preparation of 5,6:7,8:10(19)-triepoxy-9,10-secocholesta-24-enes of the formula V

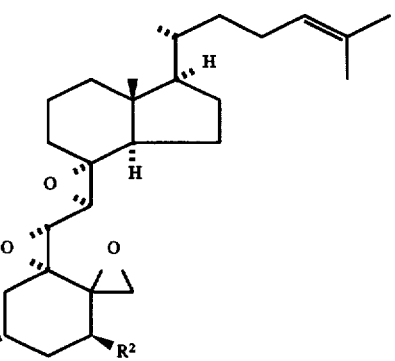

(V)

wherein

R¹ is hydrogen or a protecting group for the hydroxy function, to which R¹ is bound, R² is hydrogen or OR¹, wherein R¹ is defined above, whereby the groups R¹ and R² may be selected independently from each other, is characterized in that a compound of formula VI

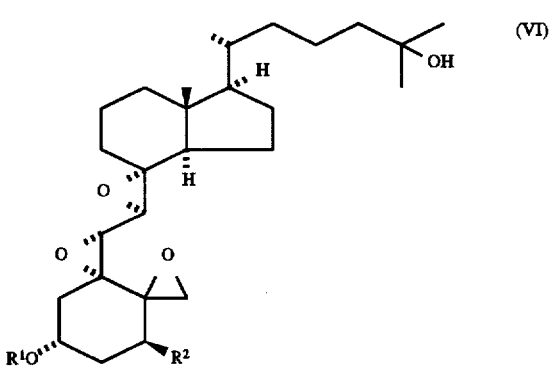

(VI)

wherein

R¹ and R² are defined above, but whereby R¹ may not be hydrogen, is reacted with a phosphorus oxychloride in pyridine at a temperature from 0° C. to 30° C. under the exclusion of water, the so obtained reaction product, with or without the removal of protecting groups R¹, is worked up, and the product of formula V is obtained.

The inventive compounds are 5,6:7,8-Diepoxy-9,10-secocholesta-10(19)-enes of the formula IV

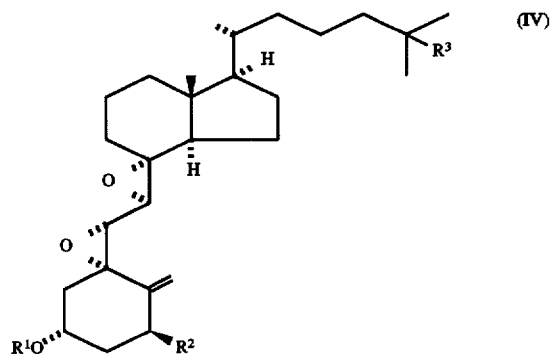

(IV)

wherein

R¹ is hydrogen or a protecting group for the hydroxy function, to which R¹ is bound, R² is hydrogen or OR¹, wherein R¹ is defined above, R³ is hydrogen or OR¹, wherein R¹ is defined above, whereby the groups R¹, R², and R³ may be selected independently from each other, but whereby R² and R³ may not be hydrogen at the same time, and
5,6:7,8:10(19)-triepoxy-9,10-secocholesta-24-enes of the formula V

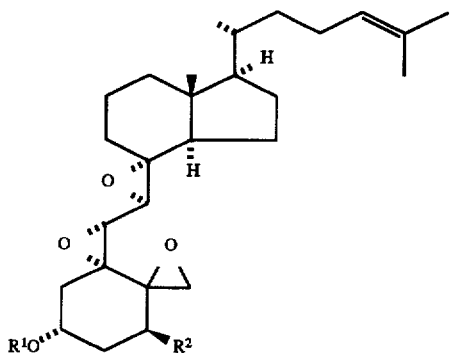

(V)

wherein
R¹ is hydrogen or a protecting group for the hydroxy function, to which R¹ is bound,
R² is hydrogen or OR¹, wherein R¹ is defined above,
whereby the groups R¹ and R² may be selected independently from each other.

Preferred embodiments of these inventive objects are defined in the dependent claims.

In the following part are described preferred embodiments of the inventive objects.

Thereby embodiments, as defined in the dependent claims, are normally not repeated.

The starting materials of formula III are prepared preferably according to the above mentioned article of R. Curci.

In preferred triepoxides of formula III R¹ is acetyl or benzoyl, R² is hydrogen and R³ is hydroxyl.

For the direct regeneration of the triene-system the 25-hydroxy group is acetylated or protected with trimethyl silane.

This acetylated or trimethylsilylated compound is then reacted with the $WCl_6$/n-butyl-lithium-system in tetrahydrofuran.

Preferably 2 to 9 moles equivalents of low-valent metal reagent are uses per mole of compound of formula III.

In this direct regeneration of the triene-system a ratio of the 5Z:5E isomers of 1:9 is obtained.

In the stepwise regeneration of the triene-system the 25-hydroxy group is acetylated after the regeneration of the 10(19)-double bond.

Also this acetylated compound is then reacted with the $WCl_6$/n-butyl-lithium-system in tetrahydrofuran.

In this stepwise regeneration of the triene-system a ratio of the 5Z:5E isomers of 3:1 is obtained.

The undesired 5E-isomer of the formula I may be separated either by chromatography or by means of the maleic anhydride method according to U.S. Pat. No. 4,554,106.

In the following scheme are summarized the reaction ways.

Scheme

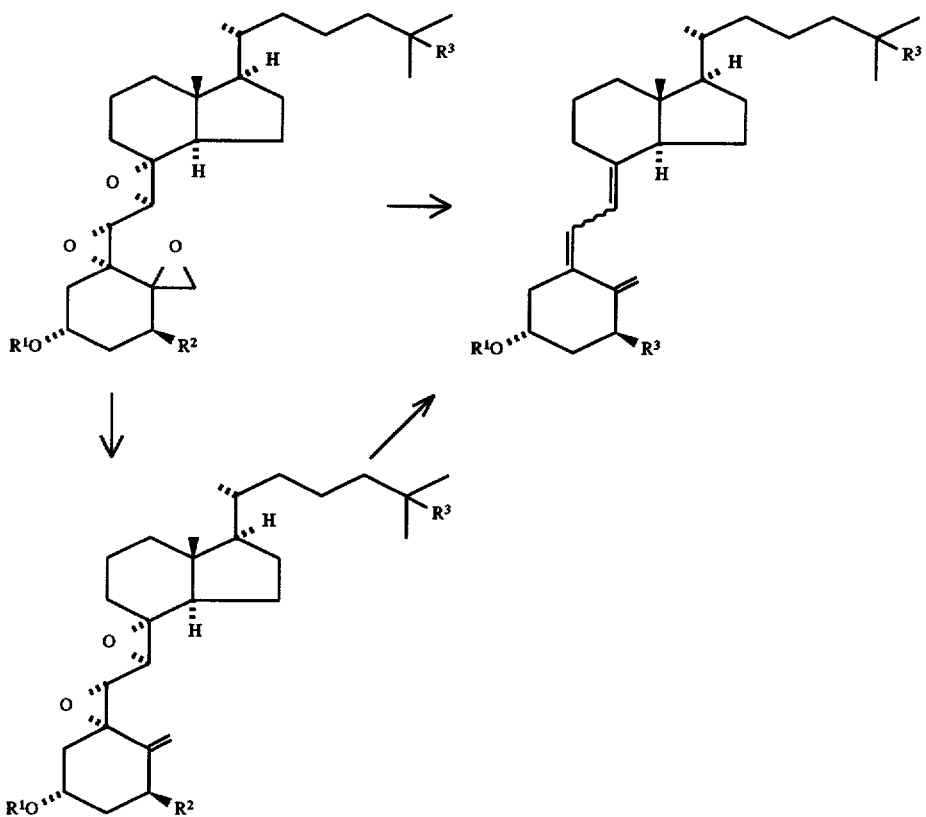

The water cleavage in the side chain of the compounds of formula VI is realized in analogy to this one mentioned in the article of L. Onisko et. al. Biochem. J. (1979) 182, 1–9 as well as B. L. Onisko et. al. Tetrahedron Letters, Nov. 13, Mar. 1977, pages 1107–1108.

In preferred starting materials of the formula VI $R^1$ is acetyl or benzoyl and $R^2$ is hydrogen.

The ratio of the 24-ene:25-ene isomers is 2:1.

The so in position 24 introduced double bond allows further modifications in the side chain.

Compounds of formula III where A and B taken together form an exocyclic methylene group of the formula =$CH_2$ are preferably produced from compounds of formula III where A and B taken together form an epoxide of the formula —(O—$CH_2$)— by reacting with a reagent in an inert gas atmosphere under the exclusion of water. One such reagent is KSeCN in a) an alcohol, preferably methanol, or b) an ether in the presence of a crown ether, preferably 18-crown-6. Another such reactant is $(R^4O)_2P(O)$—TeLi in a) an ether in the presence of a crown ether, preferably 18-crown-6, or b) $R^4OH$, where $R^4$ is an alkyl group, preferably an methyl or ethyl group. Preferred ethers are diethyl ether, dioxane, tetrahydrofuran, and dimethoxy ethane. The reaction is preferably performed under reflux.

Compounds of formula III where $R^1$ is a hydroxy protecting group, $R^2$ is a hydroxy group, $R^3$ is a hydrogen or $OR^1$, and A and B taken together form an exocyclic methylene group of the formula =$CH_2$ can also be prepared by reacting the corresponding compound of formula III where $R^2$ is hydrogen with selenium dioxide and a cooxidation agent, preferably tert-butyl-hydroperoxide or pyridinium-N-oxide, in a solvent at a temperature greater than 50° C. The solvent is either an ether, preferably dioxane, tetrahydrofuran, or dimethoxy ethane, or a hydrocarbon, preferably benzene or toluene. The reaction product is then worked up to produce the compound of formula III.

The following examples illustrate the present invention.

EXAMPLE 1

To a solution of 2 g (4.1 mmole) 3β-acetoxy-25-hydroxy-5,6:7,8:10(19)-triepoxy-9,10-secocholestane and 108 mg (0.41 mmole) 18-Crown-6 in 65 ml dry tetrahydrofuran were added 5.88 g (41 mmole) KSeCN.

This suspension was heated for 72 hours under reflux. Then the suspension was diluted with 200 ml of diethyl ether and extracted 2× with each 150 ml $H_2O$, 1× with 150 ml 1N HCl and 1× with 150 ml saturated NaCl-solution.

The organic phase was dried over $MgSO_4$, and then the solvent was distilled off.

The flash chromatography (silica gel; petroleum ether/ethylacetate 5:2) gave 920 mg (48%) pure 3β-acetoxy-25-hydroxy-5,6:7,8-diepoxy-9,10-secocholest-10(19)-ene.

$^1$H-NMR (90 MHz, $CDCl_3$, TMS): 0.63 (s, 3H, H-C(18)), 1.17 (s, 6H, H-C(26,27)), 2.00 (s, 3H, H-acetyl), 2.80 (AB, 2H, H-C(6,7)), 4.8 (m, 1H, H-C(3)), 4.94 (s.br., 1H, $H_{trans}$-C(19), 5.07 (s, hr. 1H, $H_{cis}$-C(19)).

EXAMPLE 2

A solution of 400 mg (0.84 mole) 3β-acetoxy-25-hydroxy-5,6:7,8-diepoxy-9,10-secocholest-10(19)-ene and 0.31 g (2.53 mole) p-dimethylamino pyridine in 6 ml dry $CH_2Cl_2$ was cooled to a temperature of 0° C., and 0.24 ml (2.53 mole) acetic anhydride were dropped slowly thereto.

Within 20 hours the reaction was allowed to warm to room temperature, then was diluted with 30 ml $CH_2Cl_2$ and extracted with each 30 ml saturated $NaHCO_3$-solution, 1N HCl and saturated NaCl-solution.

The organic phase was dried over $MgSO_4$, the solvent was evaporated at the rotation evaporator and it was dried under vacuum.

There were obtained 356 mg (82%) 3β,25-diacetoxy-5,6:7,8-diepoxy-9,10-secocholest10(19)-ene as a yellow sticky foam.

$^1$H-NMR (90 MHz, $CDCl_3$, TMS): 0.63 (s, 3H, H-C(18)), 1.17 (s, 6H, H-C(26,27)), 1.91 (s, 3H, H-acetyl (25)), 2.00 (s, 3H, H-acetyl(3)), 2.80 (AB, 2H, H-C(6,7)), 4.8 (m, 1H, H-C(3)), 4.93 (s, br., 1H, $H_{trans}$-C(19)), 5.07 (s, br. 1H, $H_{cis}$-C(19)).

EXAMPLE 3

There were suspended 1.07 g (2.71 mole) $WCl_6$ in 12 ml dry tetrahydrofuran and cooled to a temperature of –65° C. There were added slowly drop by drop 5.2 ml (8.13 mmole) 1.6M n-BuLi and it was allowed to warm within 30 minutes to room temperature.

Then was cooled again to a temperature of –55° C., and there was added drop by drop 200 mg (0.38 mole) 3β,25-diacetoxy-5,6:7,8-diepoxy-9,10-secocholest-10(19)-ene in 4 ml dry tetrahydrofuran.

The reaction mixture was warmed again to room temperature, and it was stirred for two hours.

Then the mixture was taken in 100 ml diethyl ether and it was extracted 2× with each 200 ml of a solution of 1.5M K/Na-tartrate in 2N NaOH and 1× with 150 ml saturated NaCl-solution.

The organic phase was dried over $MgSO_4$, the solvent was evaporated at the rotation evaporator and it was dried under vacuum.

There was obtained in this way 190 mg (100%) of a 3:1 5Z/5E mixture of 7E-3β,25-diacetoxy-9,10-secocholesta-5,7,10(19)-triene.

This mixture was distinguishable in the vinylic protons of the 5,7-diene-system in the $^1$H-NMR.

EXAMPLE 4

There were dissolved 500 mg (0.9 mole) 3β-benzoyloxy-25-hydroxy-5,6:7,8:10(19)-triepoxy-9,10-secocholestane in 35 ml absolute pyridine.

This mixture was cooled to a temperature of 0° C.

Then were added drop by drop 2.06 ml (22.5 mmole) phosphorus oxychloride. The ice bath was removed, and it was stirred for one hour at room temperature and then was cooled again to 0° C.

Then were added drop by drop 50 ml water, and it was diluted with 100 ml hexane.

Then the organic phase was extracted 4× with each 100 ml 1N HCl, 1× with 100 ml 5% $NaHCO_3$-solution and 1× with 100 ml saturated NaCl-solution.

The organic phase was dried over $MgSO_4$, and the solvent was evaporated at the rotation evaporator.

The flash chromatography (silica gel; petroleum ether/ethylacetate 7:1) gave 98 mg of a 2:1 mixture of 24-ene:25-ene of 3β-benzoyloxy-5,6:7,8:10(19)-triepoxy-9,10-secocholestane.

$^1$H-NMR (90 MHz, $CDCl_3$, TMS) of 24-ene: 3.45 (d, 1H, H-C(6 or 7)), 5.0 (m, br., 1H, H-C(24)), 5.02 (m, 1H, H-C(3)), 7.1–7.5 (m, 3H, arom. H), 7.8–8.0 (m, 2H, arom. H).

EXAMPLE 5

There were suspended 983 mg (2.48 mole) $WCl_6$ in 12 ml dry tetrahydrofuran, and it was cooled to a temperature of –65° C.

There were added slowly drop by drop 4.65 ml (7.44 mole) 1.6M n-BuLi, and it was allowed to warm within 30 minutes to room temperature.

Then was cooled again to a temperature of –55° C., and there were added drop by drop 200 mg (0.35 mole) 3β-acetoxy-5,6:7,8-diepoxy-25-trimethylsilyloxy-9,10-secocholest-10(19)-ene in 4 ml dry tetrahydrofuran.

The reaction mixture was again warmed to room temperature and stirred for two hours.

Then the mixture was taken in 100 ml diethyl ether and extracted 2× with each 150 ml of a solution of 1.5M K/Na-tartrate in 2N NaOH und 1× with 100 ml saturated NaCl-solution.

The organic phase was dried over $MgSO_4$, and the solvent was evaporated at the rotation evaporator and was dried under vacuum.

There were obtained in this way 180 mg (100%) of a 1:9 mixture of 5-cis/trans 7E-3β,acetoxy-25-trimethylsilyloxy-9,10-secocholesta-5,7,10(19)-triene, distinguishable in the vinylic protons of the 5,7-diene-system.

We claim:

1. A process for the preparation of 9,10-secocholesta-5,7,10(19)-trienes of formula (I)

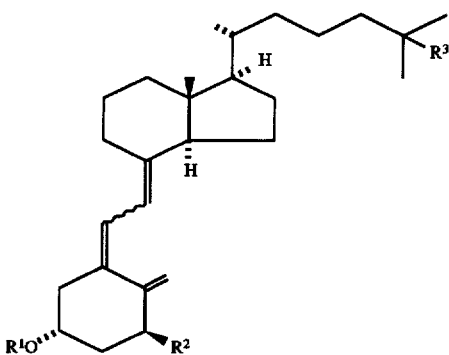

wherein $R^1$ is hydrogen or a protecting group for the hydroxy function, $R^2$ and $R^3$ are independently hydrogen or $OR^1$, comprising (a) reducing a transition metal halide of formula (II)

$$M(z)X_z \quad (II)$$

wherein

M(z) is W(VI), Nb(V), Mo(V), Ti(IV), Ti(III) or Fe(III),

X is chloride, bromide, or iodide, z is an integer from 3 to 6 and is equal to the oxidation state of the metal M with 1 to z equivalents of a reducing agent selected from an alkyl metal compound or a metal hydride to form a corresponding low-valent metal reagent under an inert atmosphere in a solvent selected from a waterfree ether or a hydrocarbon;

(b) reacting a compound of formula (III)

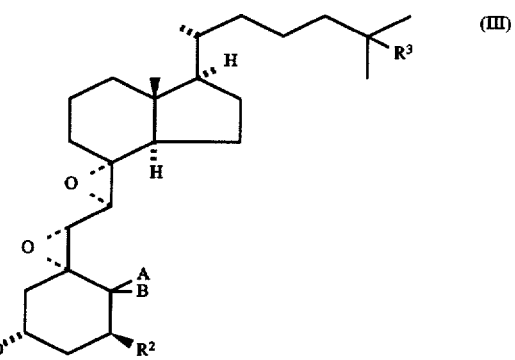

wherein $R^1$, $R^2$, and $R^3$ are as defined above,

A and B taken together are either an epoxide of the formula —(O—$CH_2$)— or an exocyclic methylene group of the formula =$CH_2$, which is dissolved a solvent selected from a waterfree ether or a hydrocarbon, with a low-valent metal reagent produced in step (a); and (c) working up the reaction product of step (b) to obtain a product of formula (I).

2. The process of claim 1 wherein the transition metal halide is a chloride.

3. The process of claim 2 wherein the transition metal halide is $WCl_6$.

4. The process of claim 1 wherein the reducing agent is n-butyl-lithium or lithium aluminum hydride.

5. The process of claim 1 wherein 2 to 4 mole equivalents of the reducing agent per mole of $WCl_6$ is employed.

6. The process of claim 1 wherein 2 to 9 mole equivalents of low-valent metal reagent per mole of compound of formula III is employed.

7. The process of claim 1 wherein the solvent is diethyl ether, dioxane, tetrahydrofuran, dimethoxy ethane, hexane, benzene, or toluene.

8. The process of claim 7 wherein the solvent is tetrahydrofuran.

9. The process of claim 6 wherein step (a) is performed at a temperature from –78° C. to room temperature.

10. The process of claim 1 wherein step (b) is performed at a temperature from –78° C. to reflux temperature.

11. The process of claim 1 wherein 2 to 9 mole equivalents of metal iodide are added to the low-valent metal reagent of step (a) prior to step (b).

12. The process of claim 11 wherein the metal iodide is an alkali metal iodide.

13. The process of claim 12 wherein the alkali metal iodide is lithium iodide.

14. The process of claim 1 wherein the protecting group for the hydroxy function is acetyl, benzyl, trimethylsilyl or tert-butyl-dimethyl-silyl.

15. The process of claim 1, wherein the compound of formula III, wherein A and B taken together are an exocyclic methylene group of the formula =$CH_2$ is produced by reacting the corresponding compound of formula III, wherein A and B taken together are an epoxide of the formula —(O—$CH_2$)— under an inert gas atmosphere and under the exclusion of water with a reagent selected from the group consisting of (I) KSeCN in (a) an alcohol, or (b) an ether in the presence of a crown ether; and (II) $(R^4O)_2P(O)$—TeLi in (a) an ether, or (b) $R^4OH$, wherein $R^4$ is an alkyl group.

16. The process of claim 15 wherein the reaction is performed under reflux.

17. The process of claim 15 wherein said alcohol is methanol.

18. The process of claim 15 wherein the ether is diethyl ether, dioxane, tetrahydrofuran or dimethoxy ethane.

19. The process of claim 15 wherein the crown ether is 18-crown-6.

20. The process of claim 15 wherein $R^4$ is ethyl or methyl.

21. The process of claim 15 wherein 1 to 10 mole equivalents of reagent per mole of compound III wherein A and B taken together form an epoxide of the formula —(O—CH$_2$)— are employed.

22. The process of claim 1, wherein the compound of formula III, wherein $R^1$ is a protecting group for the hydroxy function, $R^2$ is a hydroxy group, $R^3$ is as defined in claim 1, and A and B taken together are an exocyclic methylene group of the formula =CH$_2$, is produced by reacting a compound of formula III, wherein $R^1$, $R^3$, A and B are as defined above and $R^2$ is hydrogen, with selenium dioxide and a cooxidation agent in a solvent at a temperature greater than 50° C. and then working up the resulting product.

23. The process of claim 22, wherein the cooxidation agent is tert-butyl hydroperoxide or pyridinium-N-oxide.

24. The process of claim 22, wherein the solvent is an ether or a hydrocarbon.

25. The process of claim 24, wherein the ether is dioxane, tetrahydrofuran, or dimethoxy ethane.

26. The process of claim 24 wherein the hydrocarbon is benzene or toluene.

27. A 5,6:7,8-diepoxy-9,10-secocholesta-10(19)-ene of formula (IV)

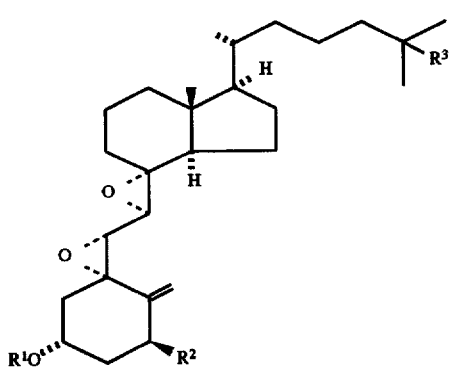

wherein $R^1$ is hydrogen or a protecting group for the hydroxy function, $R^2$ and $R^3$ are independently hydrogen or $OR^1$, provided that $R^2$ and $R^3$ are not both hydrogen.

28. A process for the preparation of 5,6:7,8:10(19)-triepoxy-9,10-secocholesta-24-enes of formula (V)

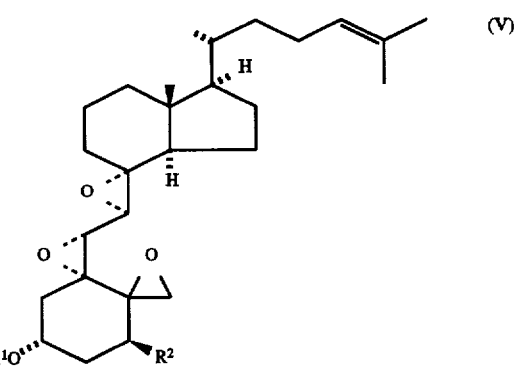

wherein $R^1$ is hydrogen or a protecting group for the hydroxy function, and $R^2$ is hydrogen or $OR^1$ comprising (a) reacting a compound of formula (VI)

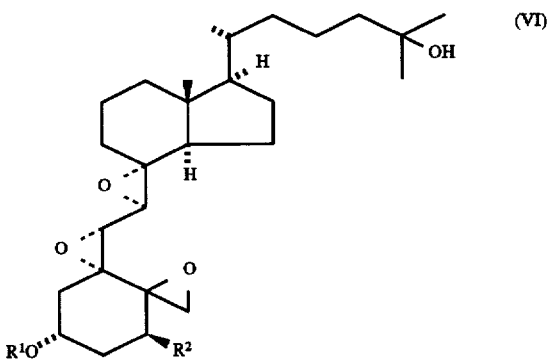

wherein $R^1$ is a protecting group for the hydroxy function and $R^2$ is hydrogen or $OR^1$ with a phosphorus oxychloride in pyridine at a temperature from 0° C. to 30° C. under the exclusion of water;

(b) optionally removing the protecting groups $R^1$; and (c) working up the resulting product.

29. A 5,6:7,8:10(19)-triepoxy-9,10-secocholesta-24-ene of formula (V)

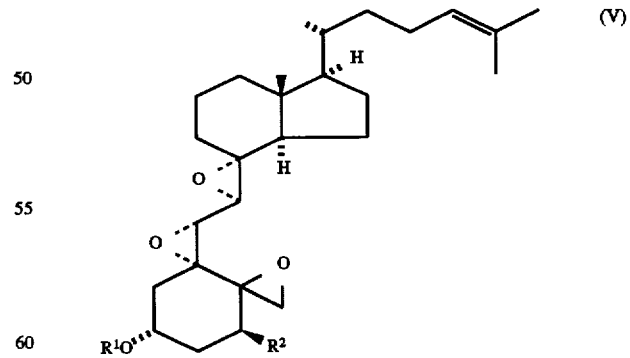

wherein $R^1$ is hydrogen or a protecting group for the hydroxy function and $R^2$ is hydrogen or $OR^1$.

* * * * *